United States Patent [19]
Goudar

[11] Patent Number: 5,756,755
[45] Date of Patent: May 26, 1998

[54] DIFLUOROMETHYLATION OF 4,5-DIHYDRO-1-PHENYL-3-METHYL-1,2,4-TRIAZOL-5(1H)-ONES WITH GLYMES AS SOLVENTS

[75] Inventor: Jaidev S. Goudar, Plainsboro, N.J.

[73] Assignee: FMC Corporation, Philadelphia, Pa.

[21] Appl. No.: 866,925

[22] Filed: May 30, 1997

Related U.S. Application Data

[60] Provisional application No. 60/026,081, Aug. 26, 1996.
[51] Int. Cl.$^6$ ................................................. C07D 249/12
[52] U.S. Cl. ............................................................ 548/263.2
[58] Field of Search ................................................ 548/263.2

[56] References Cited

U.S. PATENT DOCUMENTS 5,438,149  8/1995  Halfon et al. ...................... 548/263.2

Primary Examiner—Johann Richter
Assistant Examiner—Jane C. Osweckí
Attorney, Agent, or Firm—H. Robinson Ertelt

[57] ABSTRACT

An improved process for the difluoromethylation of a 1-(optionally substituted)phenyl-1H-1,2,4-triazol-5-one at the 4-position of the triazole ring with chlorodifluoromethane significantly reduces the cycle time required for the reaction. The improvement comprises reacting the triazolinone with potassium carbonate in a glyme solvent, heating one molar equivalent of a sodium or potassium salt of the triazolinone with 0.1 to 1 molar equivalent of potassium carbonate and 1.5 to 1.8 molar equivalents of chlorodifluoromethane in a glyme solvent, the concentration the triazolinone in the glyme being in the range of 5 to 15 percent weight/volume, at a temperature in the range of 165° to 200° C. for 5 to 30 minutes, with a 10 to 15 percent molar excess of chlorodifluoromethane, either at atmospheric pressure under an inert atmosphere or in a sealed autoclave, and recovering the difluoromethylated triazolinone.

4 Claims, No Drawings

DIFLUOROMETHYLATION OF 4,5-DIHYDRO-1-PHENYL-3-METHYL-1,2,4-TRIAZOL-5(1H)-ONES WITH GLYMES AS SOLVENTS

This application claims the benefit of Provisional Application No. 60/026,081 filed Aug. 26, 1996, pending.

The present invention relates to the haloalkylation of a triazolinone ring. In particular it discloses a method by which a difluoromethyl moiety is placed in the 4-position of a 1-(optionally substituted phenyl)-4,5-dihydro-3-methyl-5-oxo-1H-1,2,4-triazole, to provide intermediates in the routes to prepare the herbicides N-[2,4-dichloro-5-[4-(difluoromethyl)-4,5-dihydro-3-methyl-5-oxo-1H-1,2,4-triazol-1-yl]phenyl] methanesulfonamide and ethyl α-2-dichloro-5-[4-(difluoromethyl)-4,5-dihydro-3-methyl-5-oxo-1H-1,2,4-triazol-1-yl]-4-fluorobenzenepropanoate.

The process of the present invention is described by the following equation:

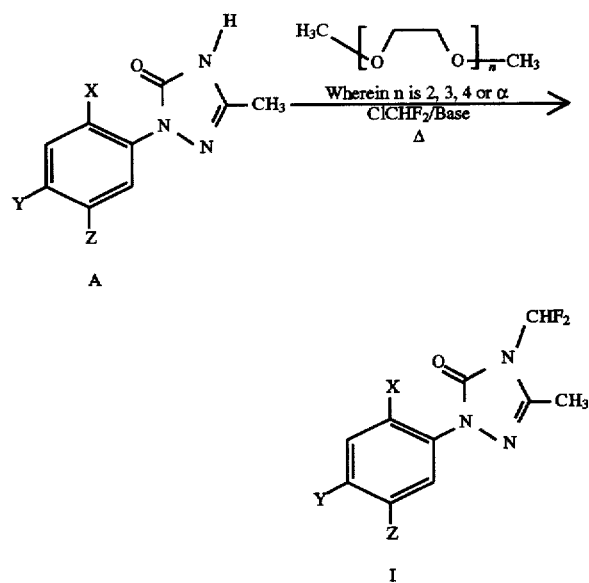

in which n equals 2 denotes diglyme, and n equals α denotes polyglyme. In the process a 1-(optionally substituted phenyl)-4,5-dihydro-3-methyl-5-oxo-1H-1,2,4-triazole I, wherein X, Y, and Z are independently selected from hydrogen, chlorine, fluorine, and nitro, is prepared by reacting triazolinone intermediate A with potassium carbonate in a glyme solvent such as tetraglyme, at a carbonate to triazolinone A ratio of 1.1 to 2 molar equivalents of carbonate to one of triazolinone; heating the reaction mixture, preferably at atmospheric pressure, to 185°–195° C., adding chlorodifluoromethane in a ratio of 1.5 to 1.8 molar equivalents of chlorodifluoromethane to one of triazolinone A, maintaining the reaction mixture at 185°–195° C. for five to 30 minutes, and recovering the difluoromethylated triazolinone I.

In an alternative method triazolinone I is prepared by reacting triazolinone intermediate A with one molar equivalent of an aqueous base, such as sodium hydroxide, in a glyme solvent, removing the water by distillation at atmospheric pressure, adding 0.25 to 0.50 molar equivalents of potassium carbonate, heating the reaction mixture to about 180° C. to drive off any remaining water, heating the reaction mixture, to about 190° C., adding chlorodifluoromethane in a ratio of about 1.5 molar equivalents of chlorodifluoromethane to one of triazolinone A, maintaining the reaction mixture at about 190° C. for five to 30 minutes, and recovering triazolinone I.

The most efficient process previously reported for carrying out this difluoromethylation reaction, disclosed in U.S. Pat. No. 5,438,149, gives significantly lower yields of the desired product when there is a substituent on the phenyl ring of the starting material triazolinone. In the prior art process the reaction of the triazolinone with potassium carbonate is carried out in a solvent such as N,N-dimethylformamide (DMF), with the necessary removal of water carried out by fractional distillation, preferably under reduced pressure. The shortest time for the distillation is given as two and a half hours. The amount of DMF removed is calculated, and an equivalent amount of DMF is added to the reaction mixture before the reaction with chlorodifluoromethane under pressure.

The process of the present invention may be carried out in a single reaction vessel at atmospheric pressure or under pressure in an autoclave. There is no requirement of lengthy fractional distillation or the special equipment needed for fractional distillation under reduced pressure. In the preferred applications of this process, the water produced by the formation of the potassium salt of the triazolinone is driven off by the high reaction mixture temperature The distillation taught in U.S. Pat. No. 5,438,149 is not required.

Thus not only does the process of the present invention give improved yields, when the starting triazolinone has a substituted phenyl ring, but the elimination of the distillation step reduces cycle time, making the process even more cost-effective.

Within the scope of the process of the present invention there are a number of experimental variations, all of which when implemented have provided excellent yields of difluoromethylated triazolinone I intermediate.

In one preferred method, one molar equivalent of a 1-(optionally substituted phenyl)-4,5-dihydro-3-methyl-5-oxo-1H-1,2,4-triazole A is stirred in a slurry of potassium carbonate in tetraglyme, either under a pressure of about 25–110 psi or at atmospheric pressure. The ratio of base used to that of triazolinone A is in the range of 0.8 to 3.0 molar equivalents of base to one molar equivalent of triazolinone A, preferably 1.1–2.0 equivalents to one. Other mild bases that have utility in the present invention include, but are not limited to, sodium bicarbonate and sodium carbonate. Diglyme and tetraglyme are the preferred solvents. When the solvent is tetraglyme, the reaction is carried out at atmospheric pressure. When the solvent is glyme, the reaction is carried out in a sealed vessel under pressure.

A useful concentration of the triazolinone A in the referred glyme solvent is in the range of 4 to 50% based on weight of triazolinone A per volume of glyme. A preferred concentration of triazolinone A in glyme is 5 to 15% weight/volume. Other glymes that have utility in the present invention include ethyl diglyme, triglyme, and polyglyme. The reaction mixture is heated to a temperature in the range of 115° to 210° C., preferably in the range of 165° to 200° C., and most preferably 180° to 195° C., during which time yield-reducing water by-product is driven off. The time required to reach the prescribed temperature is not critical, but is usually 20 to 30 minutes. Once the prescribed temperature is reached, gaseous chlorodifluoromethane is bubbled in, preferably below the surface of the reaction mixture. The ratio of chlorodifluoromethane used to that of triazolinone A is in the range of 1.1 to 4.5 molar equivalents of chlorodifluoromethane to one molar equivalent of triazolinone A, preferably 1.5–1.8 equivalents to one.

The rate of addition of chlorodifluoromethane, or the time required for completion of the addition, does not appear to be critical. However, a rate of addition in the range of about 0.1–0.2 molar equivalent/minute during a 20–30 minute period is convenient. Upon completion of the addition the reaction mixture is maintained at the most preferred temperature for 5–30 minutes, cooled to ambient temperature, and the product isolated in excellent yield by methods known to one skilled in the art. The use of catalysts such as tris(3,6-dioxaheptyl)amine (TDA-1) were of no benefit in this process step.

Examples 1 and 2 provide details on how this process is conducted.

In one variation of the method outlined above, with the same molar ratios, concentrations, reaction times, and temperatures; a solution of the triazolinone A in tetraglyme is warmed to 185° C., and four simultaneous additions, each of equimolar aliquots of potassium carbonate and chlorodifluoromethane of about 0.373 molar equivalents are added to the stirred reaction mixture, with about 10 minutes between each of the four additions. Example 4 provides details on how this process is conducted.

In another variation of the process the sodium or potassium salt of the triazolinone A is prepared by reacting the triazolinone A in a glyme solvent with about a one molar equivalent of an aqueous solution of a base such as sodium hydroxide. Preforming the salt of the triazolinone A using an aqueous base requires the removal of water from the reaction mixture prior to difluoromethylation. To remove the water, the reaction mixture temperature is brought to about 100° to 125° C., preferably to 110° to 115° C., and the water is collected by distillation at atmospheric pressure. In a manner similar to the method described above the reaction mixture temperature is then raised to about 180° to 195° C. to remove all traces of yield-reducing water. The difluoromethylation is best conducted under mildly basic conditions. This requires the addition of 0.1 to 1.0 molar equivalents, preferably 0.25 to 0.50 molar equivalents, of a base such as sodium carbonate, or preferably potassium carbonate, to the reaction mixture. The preferred concentration of the triazolinone A in the glyme solvent, and the preferred ratio of chlorodifluoromethane used to that of triazolinone A are the same as those shown above; as are the choice of solvent, reaction times, and reaction temperatures. Example 3 provides details on how this process is conducted.

Regardless of which variation of the present invention is used, high purity (87–98%) 4-difluoro-1-(optionally substituted phenyl)-4,5-dihydro-3-methyl-5-oxo-1H-1,2,4-triazole I is obtained in yields in the range of 77 to 96%. By use of the preferred processes of the present invention, the formation of the by-product O-isomer is minimal. For example, in Example 2 there is no detectable amount of the O-isomer formed.

EXAMPLE 1

Difluoromethylation of 4,5-Dihydro-1-(4-chloro-2-fluorophenyl)-3-methyl-5-oxo-1H-1,2,4-triazole in Tetraglyme under Pressure To a one liter stainless steel autoclave equipped with a mechanical stirrer, thermometer, and a gas inlet tube were added 50.0 grams (0.220 mole-1.0 equiv.) of 4,5-dihydro-1-(4-chloro-2-fluorophenyl)-3-methyl-5-oxo-1H-1,2,4-triazole and 60.8 grams (0.439 mole-2.0 equiv.) of solid potassium carbonate in 300 mL (% wt/vol. triazole to solvent—16.7%) of tetraglyme. The autoclave was sealed, and the reaction mixture was warmed to 190° C., where it stirred for 30 minutes. The pressure in the autoclave was about 28 psi. After this time 28.5 grams (0.329 mole—1.5 equiv.) of gaseous chlorodiflouromethane was bubbled in below the surface of the reaction mixture. Upon completion of the addition the reaction mixture was stirred for 30 minutes. (The pressure in the autoclave following the addition of chlorodiflouromethane was about 105 psi.) After this time the reaction mixture was cooled to ambient temperature, the autoclave was opened, and the reaction mixture was filtered to remove salt by-products. The filtrate was poured into 700 mL of water, and the resultant solid collected by filtration, washed with three 100 mL portions of water, and dried to a constant weight, yielding 57.8 grams of 89.6% pure 4-difluoromethyl-4,5-dihydro-1-(4-chloro-2-fluorophenyl)-3-methyl-5-oxo-1H-1,2,4-triazole (86.7% yield). GC analysis of the product indicated the presence of about 5.3% O-isomer by-product.

EXAMPLE 2

Difluoromethylation of 4,5-Dihydro-1-(4-chloro-2-fluorophenyl)-3-methyl-5-oxo-1H-1,2,4-triazole in Tetraglyme at Atmospheric Pressure To a two liter resin flask equipped with a condenser, mechanical stirrer, gas inlet tube, and a thermometer were added 50.0 grams (0.220 mole—1.0 equiv.) of 4,5-dihydro-1-(4-chloro-2-fluorophenyl)-3-methyl-5-oxo-1H-1,2,4-triazole and 53.1 grams (0.385 mole—1.75 equiv.) of solid potassium carbonate in 1000 mL (% wt/vol. triazole to solvent—5%) of tetraglyme. Under a nitrogen atmosphere the stirred, thickening reaction mixture was heated to 190° C., then 28.5 grams (0.330 mole—1.5 equiv.) of gaseous chlorodifluoromethane was bubbled in below the surface of the reaction mixture. The complete addition required about 20 minutes. Upon completion of the addition gas chromatographic (GC) analysis of the reaction mixture indicated 100% conversion of the triazole starting material. The reaction mixture was then allowed to cool to ambient temperature, where it stirred for about 16 hours. After this time salt by-products were removed by filtration, and the filtrate was poured into 2000 mL of water. The resultant slurry was stirred for one hour, then filtered to collect a solid, which was washed with water and dried to a constant weight, yielding 57.2 grams of 98.3% pure 4-difluoromethyl-4,5-dihydro-1-(4-chloro-2-fluorophenyl)-3-methyl-5-oxo-1H-1,2,4-triazole (92.6% yield). GC analysis of the product indicated the complete absence of any O-isomer by-product.

EXAMPLE 3

Difluoromethylation of the Sodium Salt of 4,5-Dihydro-1-(4-chloro-2-flourophenyl)-3-methyl-5-oxo-1H-1,2,4-triazole in Tetraglyme Simultaneous Addition of Base and Chlorodifluoromethane To a one liter resin flask equipped with a condenser, mechanical stirrer, gas inlet tube, Dean Stark trap, and a thermometer was added 333 mL of tetraglyme, followed by 50.0 grams (0.220 mole—1.0 equiv.) of 4,5-dihydro-1-(4-chloro-2-fluorophenyl)-3-methyl-5-oxo-1H-1,2,4-triazole (% wt/—vol. triazole to solvent—15%). A solution of 8.8 grams (0.220 mole—1.0 equiv.) of sodium hydroxide in 50 mL of water was added to the stirred mixture. The reaction mixture was then warmed to 110°–115° C. for one hour, during which time water was removed by distillation into the Dean Stark trap. Under a nitrogen atmosphere the reaction mixture temperature was raised to 180° C. to remove trace amounts of water. The reaction mixture temperature was then brought to 190° C., and 28.5 grams (0.329 mole—1.5 equiv.) of gaseous chlorodifluoro-methane was added below the reaction mixture surface, simultaneous with the addition of 15.2 grams (0.109 mole—0.5 equiv.) of powdered potassium carbonate. The complete additions required about 10 minutes. Upon completion of the additions GC analysis of the reaction mixture indicated 100% conversion of the triazole starting material. The reaction mixture was then allowed to cool to ambient temperature, after which the salt by-products were removed by filtration, and the filtrate was slowly poured into 1200 mL of water. The resultant slurry was stirred, and the solid collected by filtration. The solid was washed with water and dried to a constant weight, yielding 60.2 grams of 90.6% pure 4-difluoromethyl-4,5-dihydro-1-(4-chloro-2-fluorophenyl)-3-methyl-5-oxo-1H-1,2,4-triazole (89.3% yield). GC analysis of the product indicated the presence of about 0.23% O-isomer by-product.

EXAMPLE 4

Difluoromethylation of 4,5-Dihydro-1-(4-chloro-2-fluorophenyl)-3-methyl-5-oxo-1H-1,2,4-triazole in Tetraglyme Simultaneous Addition of Base and Chlorodifluoromethane To a one liter resin flask equipped with a cold finger, mechanical stirrer, gas inlet tube, and a thermometer was added 333 mL of tetraglyme, followed by 50.0 grams (0.220 mole—1.0 equiv.) of 4,5-dihydro-1-(4-chloro-2-fluorophenyl)-3-methyl-5-oxo-1H-1,2,4-triazole (% wt/vol. triazole to solvent—15%). Under a nitrogen atmosphere and with stirring the mixture was warmed to 185° C., and 11.4 grams (0.082 mole—0.373 equiv.) of anhydrous potassium carbonate was added in one portion. To this was then added 7.1 grams (0.082 mole—0.373 equiv.) of gaseous chlorodifluoromethane below the surface of the reaction mixture. Upon completion of the addition the reaction mixture was stirred for about 10 minutes. The sequence of potassium carbonate and chlorodifluoromethane addition was then repeated three additional times for a total addition of 1.5 molar equivalents each of potassium carbonate and chlorodifluoromethane. Upon completion of the fourth set of additions the reaction mixture was held at 185° C. for about 15 minutes. After this time GC analysis of the reaction mixture indicated 100% conversion of the triazole starting material. After the reaction mixture was cooled to ambient temperature, the salt by-products were removed by filtration, and the filtrate was slowly poured into 1200 mL of water. The resultant slurry was stirred, and the solid was collected by filtration, washed with four 100 mL portions of water, and dried to a constant weight, yielding 57.3 grams of 90.6% pure 4-difluoromethyl-4,5-dihydro-1-(4-chloro-2-fluorophenyl)-3-methyl-5-oxo-1H-1,2,4-triazole (86.3% yield). GC analysis of the product indicated the presence of about 2.9% O-isomer by-product.

EXAMPLE 5

Difluoromethylation of the Sodium Salt of 4,5-Dihydro-3-methyl-5-oxo-1-phenyl-1H-1,2,4-triazole in Tetraglyme Simultaneous Addition of Base and Chlorodifluoromethane This compound was prepared in the manner of Example 3, with 50.0 grams of 4,5-dihydro-3-methyl-5-oxo-1-phenyl-1H-1,2,4-triazole (0.286 mole—1.0 equiv.), 11.4 grams (0.286 mole—1.0 equiv.) of sodium hydroxide in 50 mL of water, 9.9 grams (0.071 mole—0.25 equiv.) of potassium carbonate, and 37.1 grams (0.429 mole—1.5 equiv.) of chlorodifluoromethane in 333 mL of tetraglyme (% wt/vol. triazole to solvent—15%) as reagents. A yield of 63.2 grams of 96.3% pure 4-difluoromethyl-4,5-dihydro-3-methyl-5-oxo-1-phenyl-1H-1,2,4-triazole (96.6% yield) was obtained. GC analysis of the product indicated the presence of about 0.9% O-isomer by-product.

EXAMPLE 6

Difluoromethylation of 4,5-Dihydro-1-(4-chloro-2-fluorophenyl)-3-methyl-5-oxo-1H-1,2,4-triazole in Polyglyme This compound was prepared in the manner of Example 1, with 25.0 grams of 4,5-dihydro-3-methyl-5-oxo-1-phenyl-1H-1,2,4-triazole (0.110 mole—1.0 equiv.), 30.0 grams (0.217 mole—2.0 equiv.) of potassium carbonate, and 14.3 grams (0.165 mole—1.5 equiv.) of chlorodifluoromethane in 220 mL of polyglyme (% wt/vol. triazole to solvent—11%) as reagents. A yield of 28.7 grams of 91.5% pure 4-difluoromethyl-4,5-dihydro-3-methyl-5-oxo-1-phenyl-1H-1,2,4-triazole (87.8% yield) was obtained. GC analysis of the product indicated the presence of about 5.0% O-isomer by-product.

EXAMPLE 7

Difluoromethylation of the Sodium Salt of 4,5-Dihydro-1-(4-chloro-2-fluorophenyl)-3-methyl-5-oxo-1H-1,2,4-triazole in Diglyme To a one liter stainless steel autoclave equipped with a mechanical stirrer, thermometer, and a gas inlet tube were placed 50.0 grams (0.20 mole—1.0 equiv.) of the sodium salt of 4,5-dihydro-1-(4-chloro-2-fluorophenyl)-3-methyl-5-oxo-1H-1,2,4-triazole and 13.8 grams (0.10 mole— 0.5 equiv.) of solid potassium carbonate in 500 mL (% wt/vol. triazole to solvent—10.0%) of diglyme. The autoclave was sealed, and the reaction mixture was warmed to 190° C. Upon reaching 190° C. the reaction vessel was vented to expel water and carbon dioxide. The reaction vessel was resealed, and 34.6 grams (0.40 mole 2.0 equiv.) of chlorodifluoromethane was bubbled in below the surface of the reaction mixture. The pressure in the autoclave following the addition of chlorodifluoromethane was about 64 psi. Upon completion of the addition the reaction mixture was maintained at 190° C. for about 30 minutes, after which the reaction mixture was cooled to ambient temperature, the autoclave was opened, and the reaction mixture was then poured into 1500 mL of water. The autoclave was rinsed with N,N-dimethylformamide, and the rinse was also added to the 1500 mL of water. The mixture was stirred vigorously for two hours, and the solid product was collected by filtration. The filter cake was washed with five 300 mL portions of water and air-dried to a constant weight, yielding 52.3 grams of 95.0% pure 4-difluoromethyl-4,5-dihydro-1-(4-chloro-2-fluorophenyl)-3-methyl-5-oxo-1H-1,2,4-triazole (89.4% yield). GC analysis of the product indicated the presence of <0.5% 0-isomer by-product.

EXAMPLE 8

Difluoromethylation of 4,5-Dihydro-1-(2,4-dichlorophenyl)-3-methyl-5-oxo-1H-1,2,4-triazole in Diglyme This compound was prepared in the manner of Example 7, with 30 grams (0.123 mole—1.0 equiv.) of 4,5-dihydro-1-(2,4-dichlorophenyl)-3-methyl-5-oxo-1H-1,2,4-triazole, 34.0 grams (0.246 mole—2.0 equiv.) of potassium carbonate, and 21.3 grams (0.246 mole—2.0 equiv.) of chlorodifluoromethane in 300 mL (% wt/vol. triazole to solvent—10.0%) of diglyme as reagents. The pressure in the autoclave was 103 psi upon completion of the addition of the chlorodifluoromethane. The yield was 32.5 grams of 90.9% pure 4-difluoromethyl-4,5-dihydro-1-(2,4-dichlorophenyl)-3-methyl-5-oxo-1H-1,2,4-triazole (87.8% yield). GC analysis of the product indicated the presence of about 1.0% O-isomer by-product.

The process of difluoromethylation in glymes is suitable for use with other 4,5-dihydro-1-phenyl-3-methyl-1,2,4-triazol-5(1 h)-ones, such as 4,5-dihydro-1-(2-fluorophenyl)-3-methyl-1H-1,2,4-triazol-5-one.

I claim:

1. In a process for the difluoromethylation of a 1-phenyl-1H-1,2,4-triazol-5-one (the triazolinone) at the 4-position of the triazole ring with chlorodifluoromethane, the improvement that comprises heating one molar equivalent of a sodium or potassium salt of the triazolinone with 0.1 to 1 molar equivalent of potassium carbonate and 1.5 to 1.8 molar equivalents of chlorodifluoromethane in a glyme solvent, the concentration the triazolinone in the glyme being in the range of 5 to 15 percent weight/volume, at a temperature in the range of 165° to 200° C. under an inert atmosphere for 5 to 30 minutes, and recovering the difluoromethylated triazolinone.

2. A process of claim 1 in which salt of the triazolinone, which may be preformed or prepared in situ, is stirred with the carbonate and a glyme selected from diglyme, tetraglyme, and polyglyme and heated to 185° to 195° C. before addition of the chlorodifluoromethane.

3. A process of claim 2 in which the reaction is carried out under autogenous pressure, and after the reaction mixture has reached 185° to 195° C., and before introduction of the chlorodifluoromethane, the pressurized container is vented before being resealed.

4. A process of claim 1 in which the triazolinone is 4,5-dihydro-1-phenyl-3-methyl-1H-1,2,4-triazol-5-one, 4,5-dihydro-1-(4-chloro-2-fluorophenyl)-3-methyl-1H-1,2,4-triazol-5-one, 4,5-dihydro-1-(2,4-dichlorophenyl)-3-methyl-1H-1,2,4-triazol-5-one, or 4,5-dihydro-1-(2-fluorophenyl)-3-methyl-1H-1,2,4-triazol-5-one.

* * * * *